United States Patent
Ishida et al.

(10) Patent No.: US 6,328,822 B1
(45) Date of Patent: Dec. 11, 2001

(54) FUNCTIONALLY GRADED ALLOY, USE THEREOF AND METHOD FOR PRODUCING SAME

(75) Inventors: Kiyohito Ishida, 5-20 Kamisugi 3-chome, Aoba-ku, Sendai-shi, Miyagi-ken; Yoshikazu Ishii, 1-1 Shinmachi 5-chome, Houya-shi, Tokyo; Ryosuke Kainuma, Miyagi-ken, all of (JP)

(73) Assignees: Kiyohito Ishida, Sendai; Yoshikazu Ishii, Houya, both of (JP)

( * ) Notice: Subject to any disclaimer, the term of this patent is extended or adjusted under 35 U.S.C. 154(b) by 0 days.

(21) Appl. No.: 09/339,929

(22) Filed: Jun. 25, 1999

(30) Foreign Application Priority Data

Jun. 26, 1998 (JP) .................................................. 10-181268
Jul. 3, 1998 (JP) .................................................. 10-189489
Jul. 3, 1998 (JP) .................................................. 10-189490

(51) Int. Cl.[7] .............................. C22C 9/01; C22C 9/05; A61M 25/09
(52) U.S. Cl. .......................... 148/436; 148/402; 148/563; 428/547; 428/610; 428/694 GR
(58) Field of Search .................................... 148/436, 402, 148/563; 428/547, 610, 694 GR

(56) References Cited

U.S. PATENT DOCUMENTS 4,925,445 5/1990 Sakamoto et al. .
5,596,996 1/1997 Johanson et al. .

FOREIGN PATENT DOCUMENTS

250952 * 10/1987 (DD) .
2919478 * 11/1980 (DE) .

(List continued on next page.)

OTHER PUBLICATIONS

Kaps, Reinhard; Ruddeck, Peter; Eberlein, Juergen; Warren, Betriebsteil; Wagner, Ingeberg, Structure and Properties of Cast Copper–Aluminum Alloys, Giessereitechnik (1985), 31(10), 320–1 (Provided Abstract Only).*
Nesterenko, E. G.; Osipenko, I. A, Low Temperature Segregation in Copper–Manganese–Aluminum Alloys with Different Degrees of Deviation from Stoichiometric Composition, Fiz. Metal. Metalloved. (1973), 36 (4), 702–10 (Submitted Abstract Only).
Kainuma, Ryosuke; Sato, Naoya; Ishida, Kiyohito, Phase Stability and Mechanical Properties of Cu–Al–Mn Heusler Alloys, Shindo Gijutsu Kenkyu Kaishi (1996), 35, 211–215 (Applicants Provided Abstract Only).
XP–002117067 Chemical Abstracts, vol.80, No. 12, Mar. 25, 1974 Nesterenko et al., "Low–temperature segregation in copper–manganese–aluminum alloys with different degrees of deviation from stoichiometric composition" AN 80: 62692 HCA.
XP–002117068 Chemical Abstracts, vol.127, No.9, Sep. 1, 1997, Kainuma et al., "Phase stability and mechanical properties of Cu–Al–Mn Heusler alloys" AN 127: 124857 HCA.

Primary Examiner—Sikyin Ip

(57) ABSTRACT

The functionally graded alloy having a composition comprising 3–10 weight % of Al, 5–20 weight % of Mn, the balance being substantially Cu and inevitable impurities has a first portion composed essentially of a β-phase, a second portion composed essentially of an α-phase and a Heusler phase, and a third portion having a crystal structure changing continuously or stepwise from the first portion to the second portion. The functionally graded alloy can be produced by forming a copper-based alloy having the above composition, keeping it at 500° C. or higher and rapidly cooling it, and then subjecting it to an aging treatment by a gradient temperature heater. Such functionally graded alloy can suitably be used for guide wires and catheters.

6 Claims, 10 Drawing Sheets

FOREIGN PATENT DOCUMENTS

| | | |
|---|---|---|
| 224549 | 5/1990 | (JP) . |
| 4 365827 | 12/1991 | (JP) . |
| 4 28375 | 1/1992 | (JP) . |
| 5278158 | 10/1993 | (JP) . |
| 762472 | 3/1995 | (JP) . |
| 98/19728 | 5/1998 | (WO) . |

* cited by examiner

FUNCTIONALLY GRADED ALLOY, USE THEREOF AND METHOD FOR PRODUCING SAME

BACKGROUND OF THE INVENTION

The present invention relates to a copper-based, functionally graded alloy having uniform composition and diameter and continuously or stepwise changing properties such as hardness, modulus elongation, etc. and a method for producing such an alloy, and use of such an alloy in guide wires, catheters, etc.

Functionally graded alloys are materials having continuously or stepwise changing properties such as hardness, elasticity, thermal conductivity, electric conductivity, etc. without gradient in size given by mechanical working such as cutting, etc. or chemical treatments such as etching, etc. Functionally graded materials developed so far are mostly such two-component composites as SiC/C, ZrO/W, TiC/Ni, ZrO/Ni, etc., which have gradually changing mixing ratios.

Conventional functionally graded materials having gradually changing mixing ratios have been produced by mixing different material powders at gradually changing mixing ratios to prepare a plurality of mixed powder sheets having gradually changing mixing ratios, laminating the mixed powder sheets along the gradually changing mixing ratios, compacting and sintering them. For example, Japanese Patent Laid-Open No. 5-278158 discloses a functionally graded, binary metal material produced by laminating and sintering W powder and Mo powder at a gradually changing mixing ratio.

However, the functionally graded materials produced by such a method cannot be rolled or drawn, and they can be formed to desired shapes only by cutting. Thus, they are not only very expensive but also cannot be formed into complicated shapes. Accordingly, the conventional functionally graded materials are used mainly in highly expensive applications, such as spacecraft, nuclear power generators, etc. It is thus highly desired to develop less expensive and easy-to-form functionally graded materials.

Also, alloys having shape recovery properties and superelasticity are widely used in various applications such as guide wires, catheters, etc. To introduce the catheter into the blood vessel and place it at a desired site in the blood vessel, a guide wire for guiding the catheter is first introduced into the desired site in the blood vessel, and the catheter is guided to the desired site in the blood vessel along the guide wire. Because human blood vessels are winding and branching differently depending on individuals, guide wires having high introduction operability and torque conveyance are required to insert the guide wires without damaging the blood vessel walls.

For this purpose, the guide wire is composed of a core wire comprising a tip end portion which is made soft by reducing its diameter, and a body portion which is relatively rigid, and a coating layer formed on the core wire, the coating layer being made of synthetic resins which do not cause any damage to the human body, such as polyamides, thermoplastic polyurethanes, fluoroplastics, etc.

The guide wire is usually constituted by a coil-shaped metal wire made of stainless steel, carbon steel, etc. However, wires of such materials are easily bent, superelastic metals such as Ni—Ti alloys, etc. are used for the core wires of the guide wires (Japanese Patent Publication No. 2-24549).

However, because superelastic Ni—Ti alloys lack rigidity, though they are sufficiently soft. Therefore, they are not well inserted into the blood vessel, sometimes making it difficult to place them at a desired place in the blood vessel.

Also, because Ni—Ti alloys are relatively poor in cold working, they are not easily formed into thin wires suitable for guide wires, etc. With respect to the gradient of properties by heat treatment, it is difficult to provide the guide wire with such a gradient as to control the torque conveyance of the guide wire.

The same is true of catheters made of Ni—Ti alloys. The Ni—Ti alloy catheters are not well inserted into the blood vessel. Also, Ni—Ti alloys are not easily formed into thin wires or pipes. Further, the Ni—Ti alloys are poor in weldability and adhesion, posing problems when combined with other materials.

OBJECT AND SUMMARY OF THE INVENTION

An object of the present invention is to provide an inexpensive functionally graded alloy having excellent workability and a method for producing such a functionally graded alloy.

Another object of the present invention is to provide a core wire for a guide wire comprising a soft tip end portion and a properly elastic and rigid body portion, excellent in insertion operability, torque conveyance, and workability, and a guide wire comprising such a core wire.

A further object of the present invention is to provide a catheter comprising a soft tip end portion and a properly elastic and rigid body portion, excellent in insertion operability, torque conveyance, and workability.

As a result of research on the previously proposed shape memory Cu—Al—Mn alloy having a $\beta$-phase structure (Japanese Patent Laid-Open No. 7-62472), the inventors have found that when the shape memory Cu—Al—Mn alloy having a $\beta$-phase structure is partially heated at particular temperatures or at gradually changing temperatures, the shape memory Cu—Al—Mn alloy is provided with a partially different crystal structure, which shows remarkably gradient properties. The inventors have also found that by giving gradually changing properties to the Cu—Al—Mn alloy by a heat treatment at a proper temperature gradient, the guide wire and the catheter can be produced from such Cu—Al—Mn alloy with extremely improved insertion operability and torque conveyance. The present invention has been completed based upon these findings.

The functionally graded alloy of the present invention has a composition comprising 3–10 weight % of Al, 5–20 weight % of Mn, the balance being substantially Cu and inevitable impurities, and comprises a first portion composed essentially of a $\beta$-phase, a second portion composed essentially of an $\alpha$-phase and a Heusler phase, and a third portion having a crystal structure continuously or stepwise changing from the first portion to the second portion.

The method for producing the functionally graded alloy according to the present invention comprises the steps of:

(a) forming a copper-based alloy having a composition comprising 3–10 weight % of Al, 5–20 weight % of Mn, the balance being substantially Cu and inevitable impurities, into a desired shape;

(b) keeping the copper-based alloy at 500° C. or higher and rapidly cooling it to transform a crystal structure thereof substantially to a $\beta$-phase; and (c) subjecting the copper-based alloy to an aging treatment by a heater having a temperature gradient, thereby heating the first portion to lower than 250° C., the second portion to 250–350° C., and the third portion at a temperature continuously or stepwise changing from the heating temperature of the first portion to the heating temperature of the second portion.

The core wire for a guide wire according to the present invention comprises a body portion having high rigidity and a tip end portion having a lower rigidity than that of the body portion, at least part of the core wire being made of a copper-based alloy comprising 3–10 weight % of Al, and 5–20 weight % of Mn, the balance being substantially Cu and inevitable impurities.

The guide wire according to the present invention comprises a core wire comprising a body portion having high rigidity and a tip end portion having a lower rigidity than that of the body portion, at least part of the core wire being made of a copper-based alloy comprising 3–10 weight % of Al, and 5–20 weight % of Mn, the balance being substantially Cu and inevitable impurities.

The catheter according to one embodiment of the present invention is at least partially constituted by a metal pipe, the metal pipe being, at least in a tip end portion, made of a copper-based alloy comprising 3–10 weight % of Al, and 5–20 weight % of Mn, the balance being substantially Cu and inevitable impurities.

The catheter according to another embodiment of the present invention contains a reinforcing metal member in at least part of a catheter tube, the reinforcing metal member being made of a copper-based alloy comprising 3–10 weight % of Al, and 5–20 weight % of Mn, the balance being substantially Cu and inevitable impurities.

DETAILED DESCRIPTION OF THE PREFERRED EMBODIMENTS

[1] Composition of Functionally Graded Alloy

Figure 1:
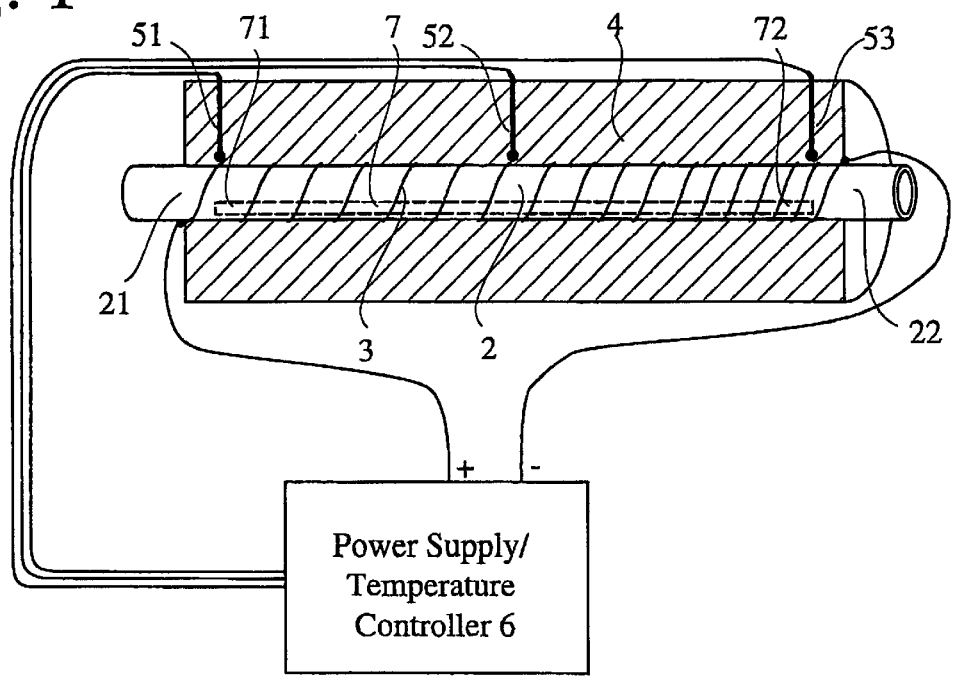
FIG. 1 is a schematic view showing an example of gradient temperature beater.

The functionally graded alloy of the present invention contains 3–10 weight % of Al, 5–20 weight % of Mn, and the balance being substantially Cu and inevitable impurities. Though the functionally graded alloy has β-phase structure [body-centered cubic (bcc) structure] at a high temperature, a martensitic transformation without diffusion occurs at a low temperature. Specifically, the β-phase structure is changed to a dual-phase structure of an α-phase [face-centered cubic (fcc) structure] and a Heusler phase [ordered body-centered cubic (fcc) structure] by beating at about 300° C.

When the Al content is less than 3 weight %, the β-phase cannot be formed. On the other hand, when it exceeds 10 weight %, the resultant alloy becomes extremely brittle. The preferred Al content is 6–10 weight %, though it may be changed depending on the amount of Mn.

The inclusion of Mn makes the range of the β-phase shift toward a low Al region, thereby remarkably improving the cold workability of the alloy, which makes it easy to form the alloy. When the content of Mn is less than 5 weight %, sufficient workability cannot be obtained, failing to form the region of the β-phase. On the other hand, when the content of Mn exceeds 20 weight %, sufficient shape recovery properties cannot be obtained. The preferred content of Mn is 8–12 weight %.

The Cu—Al—Mn alloy having the above composition has good hot- and cold-workability, achieving a cold working ratio of 20 to 90% or more. This enables the formation of extremely thin wires, sheets, pipes, etc., which is conventionally difficult.

In addition to the above components, the functionally graded alloy of the present invention may further contain at least one metal selected from the group consisting of Ni, Co, Fe, Ti, V, Cr, Si, Nb, Mo, W, Sn, Ag, Mg, P, Zr, Zn, B, and misch metals. These elements act to make crystal grains fine while maintaining the cold workability of the functionally graded alloy, thereby improving the strength of the alloy. The total content of these additional elements is preferably 0.001–10 weight %, particularly 0.001–5 weight %. When the total content of these elements exceeds 10 weight %, the martensitic transformation temperature of the alloy lowers, making the β-phase structure unstable.

Ni, Co, Fe and Sn are elements effective for strengthening the matrix structure of the alloy. The preferred content is 0.001–3 weight % for each of Ni and Fe. Though Co acts to make crystal grains fine by the formation of Co—Al, an excess amount of Co reduces the toughness of the alloy. Thus, the preferred content of Co is 0.001–2 weight %. Also, the preferred content of Sn is 0.001–1 weight %.

Ti is combined with harmful elements such as N and O to form oxynitrides. When Ti is added together with B, they form borides which function to make crystal grains fine, thereby improving the shape recovery ratio of the alloy. The preferred content of Ti is 0.001–2 weight %.

V, Nb, Mo and Zr act to increase the hardness of the alloy, thereby improving the wear resistance of the alloy. Because these elements are not substantially dissolved in the matrix, they are deposited as bcc crystals, effective in making the crystal grains fine. The preferred content of each of V, Nb, Mo and Zr is 0.001–1 weight %.

Cr is an element effective in maintaining the wear resistance and the corrosion resistance of the alloy. The preferred content of Cr is 0.001–2 weight %.

Si acts to increase the corrosion resistance of the alloy. The preferred content of Si is 0.001–2 weight %.

W acts to improve the deposition strengthening of the alloy because W is not substantially dissolved in the matrix. The preferred content of W is 0.001–1 weight %.

Mg acts to remove harmful elements such as N and O and fix harmful S as sulfides, thereby improving the hot workability and the toughness of the alloy. However, an excess amount of Mg causes the grain boundary segregation, thereby making the alloy brittle. The preferred content of Mg is 0.001–0.5 weight %.

P acts as a deoxidizer, improving the toughness of the alloy. The preferred content of P is 0.01–0.5 weight %.

Zn acts to lower the shape memory treatment temperature. The preferred content of Zn is 0.001–5 weight %.

B, which acts to make crystal grains fine, is preferably used together with Ti and Zr. The preferred content of B is 0.01–0.5 weight %.

Misch metals act to make crystal grains fine. The preferred content of misch metals is 0.001–2 weight %.

[2] Production of Functionally Graded Alloy (a) Forming of copper-based alloy

A melt of the copper-based alloy having the composition mentioned above is cast and formed into a desirable shape by hot rolling, cold rolling, pressing, etc. The alloy of the present invention has good hot and cold workability, achieving a cold working ratio of 20 to 90% or more. This enables the formation of extremely thin wires, sheets, ribbons, pipes, etc. which is conventionally difficult.

In the case of the copper-based alloy containing 8–10 weight % of Al, the α+β dual-phase structure having excellent workability is formed when the average cooling speed after hot working is 200° C./minute or less. The copper-based alloy is desirably cooled at the above speed particularly in a range of 800–400° C. If the cooling speed is faster than the above speed, the β-phase is mainly formed in the alloy, failing to obtain as high workability as when the α+β dual-phase is formed. On the other hand, in the case of the copper-based alloy containing 3–8 weight % of Al, the copper-based alloy may be composed only of a β-phase structure after hot working, and the cooling speed after hot working is not limited.

(b) Solution treatment

The copper-based alloy is then subjected to a heat treatment (solution treatment) at 500° C. or higher, preferably 600–900° C. to transform its crystal structure to the β-phase. After heat treatment, the β-phase is frozen by rapid cooling at a rate of 50° C./second or more. The rapid cooling of the alloy is carried out by immersing in a cooling medium such as water or by forced-air cooling. When the cooling speed is lower than 50° C./second, The deposition of the α-phase takes place in the alloy, failing to maintain the alloy in a state having only the β-phase crystal structure and thus reducing the property gradient. The preferred cooling speed is 200° C./second or more.

(c) Aging treatment

According to the present invention, the aging treatment of the first portion where the β-phase crystal structure is maintained is carried out at a temperature of lower than 250° C. The aging treatment of the second portion where the crystal structure is transformed into the dual-phase structure of the α-phase and the Heusler phase is carried out at 250–350° C. The aging treatment of the third portion between the first and second portions is carried out at a continuous or stepwise temperature gradient (temperature distribution) from the heating temperature of the first portion to that of the second portion.

To meet the above conditions, the aging treatment is preferably carried out in a gradient temperature heater. FIG. 1 is a schematic view showing an example of such a gradient temperature heater. The gradient temperature heater 1 for the aging treatment of a functionally graded alloy rod 7 comprises a furnace pipe 2, a nichrome wire 3 wound around the furnace pipe 2, a heat-insulating member 4, a plurality of temperature sensors 51, 52, 53 and a power supply/temperature controller 6 connected to the nichrome wire 3 and the temperature sensors 51, 52, 53. In this example, the density gradient of the wound nichrome wire 3 decides the temperature gradient in the furnace pipe 2. To turn one end portion 71 of the alloy rod 7 to a first portion composed essentially of a β-phase, the nichrome wire 3 is wound sparsely around one end portion 21 of the furnace pipe 2. Also, to turn the other end portion 72 of the alloy rod 7 to a second portion composed essentially of an α-phase and a Heusler phase, the wire 3 is wound densely around the other end portion 22 of the furnace pipe 2. Thus, the furnace pipe 2 has a temperature gradient which may be controlled by the power supply/temperature controller 6.

The heating temperature of the first portion is lower than 250° C., preferably 100–200° C. If the heating temperature of the first portion were too low, the β-phase would be unstable, making it likely for the martensitic transformation temperature to change when left at room temperature. On the other hand, when the heating temperature is 250° C. or higher, the α-phase may be deposited, failing to increase the difference in properties between the first and second portions.

The heating temperature of the second portion is 250–350° C., preferably 280–320° C. When it is lower than 250° C., the crystal structure of the second portion is not sufficiently transformed into a dual-phase structure of an α-phase and a Heusler phase, failing to increase the difference in properties between the first and second portions. On the other hand, when it is higher than 350° C., the crystal structure becomes coarse, deteriorating such properties as yield stress, hardness, etc.

The difference in heating temperature between the first and second portions is preferably 50° C. or higher, particularly 80° C. or higher. When it is lower than 50° C., The difference in properties between the first and second portions becomes smaller.

The aging treatment time in general is preferably 1–300 minutes, particularly 5–200 minutes, though it may vary depending on the composition of the functionally graded alloy. Less than 1 minute of aging would not provide sufficient aging effects. On the other hand, when the aging time is longer than 300 minutes, the alloy structure becomes too coarse to keep sufficient mechanical properties as the functionally graded material.

In the case of the core wire for a guide wire, the copper-based alloy core wire may be subjected to an aging treatment in the following two ways: The first aging treatment is to heat the core wire uniformly at 250° C. or lower, preferably 100–200° C., such that it has shape recovery properties and superelasticity uniformly.

The second aging treatment is to heat the core wire at different temperatures, such that the core wire has gradient properties. Namely, the core wire has a high-rigidity body portion, a low-rigidity tip end portion, and an intermediate portion between them having rigidity decreasing from the high-rigidity body portion to the low-rigidity tip end portion. The high-rigidity body portion is obtained by an aging treatment at 250–350° C., preferably 280–320° C., and the low-rigidity tip end portion is obtained by an aging treatment at lower than 250° C., preferably 100–200° C. The intermediate portion between them is obtained by an aging treatment at a temperature continuously or stepwise changing from the high-rigidity body portion to the low-rigidity tip end portion. The difference in aging temperature between the high-rigidity body portion and the low-rigidity tip end portion is preferably 50° C. or higher, particularly 80° C. or higher.

[3] Properties of Functionally Graded Alloy
(1) Crystal structure

The functionally graded alloy of the present invention comprises a first portion composed essentially of β-phase, a second portion composed essentially of an α-phase and a Heusler phase, and a third portion having a crystal structure continuously or stepwise changing from the first portion to the second portion.

The term "composed essentially of a β-phase" used herein means not only a crystal structure consisting only of a β-phase, but also a crystal structure containing, in addition to the β-phase, other phases such as an α-phase, a Heusler phase, borides such as TiB and ZrB, bcc phases of V, Mo, Nb and W, and intermetallic compounds such as NiAl, CoAl, etc. in such small percentages as not to affect the superelasticity and shape recovery properties of the first portion. The total amount of the α-phase and the Heusler phase is preferably 5 volume % or less. When it exceeds 5 volume %, the superelasticity and shape recovery properties of the first portion are remarkably decreased, thereby making the gradient of properties smaller.

Also, the term "composed essentially of a dual-phase of an α-phase and a Heusler phase" used herein means not only a crystal structure consisting of only the α-phase and the Heusler phase, but also a crystal structure containing, in addition to the α-phase and the Heusler phase, other phases such as β-phase, borides such as TiB and ZrB, bcc phases of V, Mo, Nb and W, and intermetallic compounds such as NiAl, CoAl, etc. in such small percentages as not to affect the hardness of the second portion. The amount of the β phase is preferably 10 volume % or less in the second portion.

The term "continuously or stepwise changing crystal structure" used herein means that a volume ratio of the β-phase to [the α-phase+the Heusler phase] changes continuously or stepwise in the crystal structure. The α-phase and the Heusler phase may be gradually deposited from the β-phase by aging treatment. The higher the aging temperature, and the longer the aging time, the more the α-phase and the Heusler phase are deposited. Whether the crystal structure changes continuously or stepwise in the third portion depends upon the aging temperature distribution and the aging time. When the aging treatment is carried out at a stepwise temperature distribution for a short period of time, the resultant crystal structure changes stepwise. The boundaries between the first and third portions and between the second and third portions are not explicit in the case of the third portion having a continuously changing crystal structure. Because the properties change generally sharply in the third portion, however, the boundaries of the above three portions can relatively easily be determined from the distribution of properties.

The first portion composed essentially of the β-phase has shape memory properties and superelasticity as described in Japanese Patent Laid-Open No. 7-62472. In contrast, the second portion is composed of a hard material resistant to bending and having completely different properties from those of the first portion. The properties change continuously or stepwise in the third portion from those of the first portion to those of the second portion. Though the distance between the first portion and the second portion (length of the third portion) may arbitrarily be set, it is preferably about 2 cm or more, particularly about 5 cm or more. It is difficult to provide the aging temperature gradient in a distance of less than 2 cm.
(2) Differences in properties With respect to some properties, differences between the first portion and the second portion will be described in detail below.
(a) Hardness The first portion preferably has a hardness of less than 350 Hv, and the difference in hardness between the first portion and the second portion can be made as large as 20 Hv or more, though the hardness of the alloy may vary within the above range depending on its composition.
(b) Yield stress Because the first portion composed essentially of a β-phase has superelasticity, the yield stress (0.2% offset yield strength) of the first portion is less than 400 MPa, though it may vary within this range depending upon the composition of the alloy. The difference in yield stress between the first portion and the second portion can be made as large as 50 MPa or more.
(c) Shape recovery ratio The first portion has excellent shape recovery properties, showing a shape recovery ratio of 80% or more, while the shape recovery ratio of the second portion is as low as less than 15%, which means substantially no shape recovery properties. The difference in shape recovery ratio between the first and second portions can be made as large as 70% or more.

[4] Core Wire for Guide Wire

The core wire for a guide wire is constituted by a functionally graded copper-based alloy wire having at least a low-rigidity tip end portion and a high-rigidity body portion.

(1) First Embodiment

Figure 7:
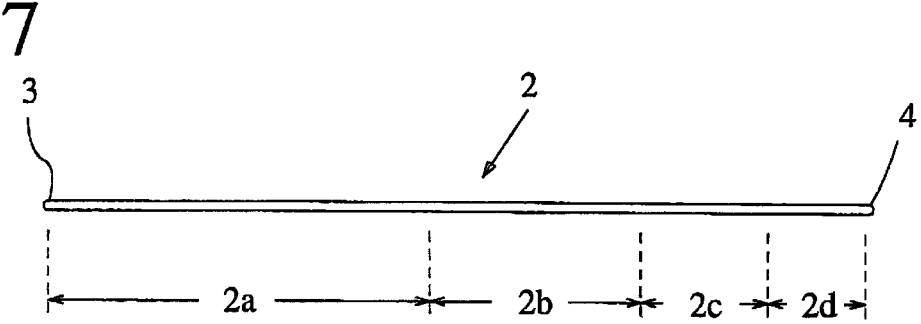
FIG. 7 is a schematic view showing one example of the core wire for a guide wire according to the present invention.

In the first embodiment as shown in FIG. 7, the core wire is a straight copper-based alloy wire having a tip end portion that is not tapered. The core wire 2 is composed of four regions 2a, 2b, 2c and 2d from the base end 3 to the tip end 4, and each region 2a, 2b, 2c and 2d has rigidity decreasing stepwise from the side of the base end 3 to the side of the tip end 4. Each region may have an arbitrarily set length.

Such gradient-rigidity core wire may be formed, as described above, by hot working and/or cold working, keeping at 500° C. or higher and rapidly quenching, and further aging treatment at different temperatures in respective regions 2a, 2b, 2c and 2d. The aging temperature in the region 2a is preferably 250–350° C., and the aging temperature in the region 2d is lower than 250° C. The aging temperatures in the regions 2b and 2c are between those for the regions 2a and 2d, with the aging temperature in the region 2b higher than that for the region 2c.

(2) Second Embodiment

Figure 8:
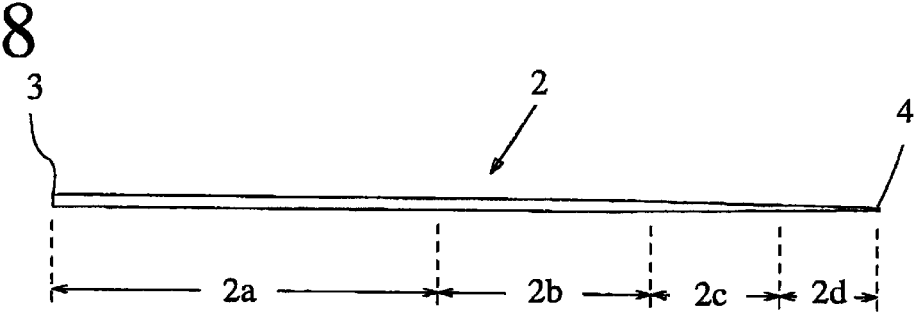
FIG. 8 is a schematic view showing another example of the core wire for a guide wire according to the present invention.

In the second embodiment as shown in FIG. 8, the core wire is a copper-based alloy wire composed of four regions 2a, 2b, 2c and 2d from the base end 3 to the tip end 4, with a taper from the region 2c to the tip end 4. Rigidity decreases in each region 2a, 2b, 2c and 2d from the side of the base end 3 to the side of the tip end 4. Each region may have an arbitrarily set length.

Like the first embodiment, the region 2a is a high-rigidity region, while the region 2d is a low-rigidity region. The regions 2b and 2c have intermediate rigidity between that of the regions 2a and 2d, with the rigidity of the region 2b higher than that of the region 2c. Because the region 2d has a smaller diameter in the second embodiment than in the first embodiment, the softness of the copper-based alloy in the region 2d may be less in the second embodiment than in the first embodiment. The core wire of the second embodiment may be produced in the same manner as in the first embodiment.

(3) Third Embodiment

Figure 9:
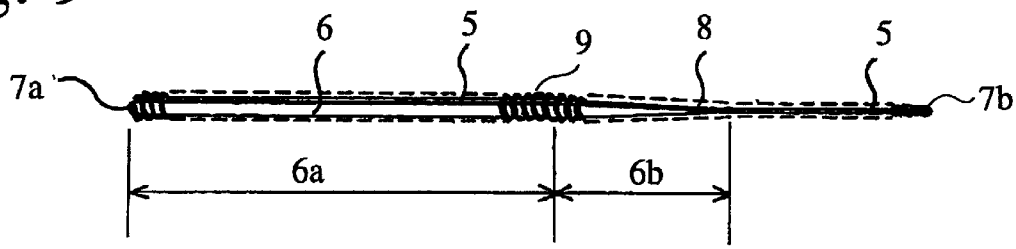
FIG. 9 is a schematic view showing one example of the guide wire according to the present invention.

In the third embodiment as shown in FIG. 9, the core wire is constituted by a base wire 5 and a core wire 6 connected to each other. The core wire 6 is a copper-based alloy wire, and the base wire 5 may be a flat ribbon made of known materials such as stainless steel. Ends of the base wire 5 and the core wire 6 are partially overlapped and bonded with a coil, etc.

The core wire 6 consists of two regions 6a, 6b from the base end 7a to the tip end 7b. The region 6a is a high-rigidity region, while the region 6b is a region having rigidity continuously decreasing toward the tip end 7b. The core wire 6 is soft (less rigid) and superelastic in the vicinity of the tip end 7b. Each region may have an arbitrarily set length.

Like the first embodiment, the core wire 6 is provided with rigidity gradient by different aging treatment temperatures applied to respective regions. The aging temperature of the region 6a is preferably 250–350° C. Also, the aging temperature of the region 6b has a temperature distribution continuously lowering from the base end 7a to the tip end 7b. The highest temperature of the above temperature distribution is preferably the same as in the region 6a, and the lowest temperature in the region 6b is preferably lower than 250° C.

[5] Catheter (a) Catheter having copper-based alloy pipe

The first catheter of the present invention is at least partially constituted by a copper-based alloy pipe. The catheter is relatively rigid in a body portion, and has low rigidity in a tip end portion. The bending modulus of the copper-based alloy pipe decreases continuously or stepwise in a direction from the base end to the tip end of the catheter, and at least a tip end portion of the copper-based alloy pipe has superelasticity. The followings are specific examples of such catheters.

(i) First embodiment

Figure 14:
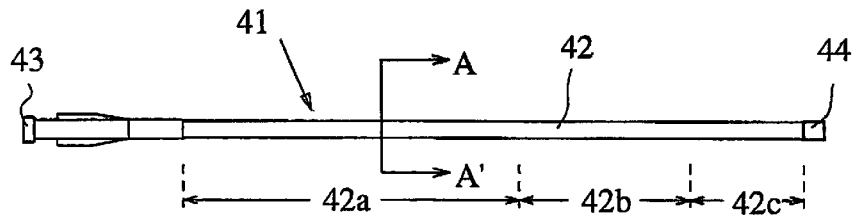
FIG. 14 is a schematic view showing an example of the catheter according to the present invention.
Figure 15:
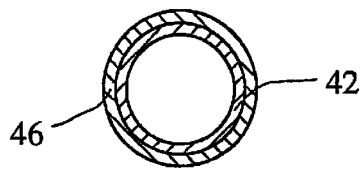
FIG. 15 is an enlarged A–A' cross-sectional view of FIG. 14.

FIG. 14 shows the first example of the catheter of the present invention, and FIG. 15 is an A–A' cross-sectional view of FIG. 14.

A body of the catheter 41 is constituted by a copper-based alloy pipe 42, which has bending modulus decreasing continuously or stepwise from the base end 43 to the tip end portion 44. The copper-based alloy pipe can be formed from a thicker pipe by gradually reducing its diameter by rolling or drawing.

The pipe 42 has a high-rigidity body portion 42a, a low-rigidity, superelastic tip end portion 42c and an intermediate portion 42b between them having intermediate rigidity. In each region, rigidity may be uniform or gradually changing.

Such a gradient rigidity copper-based alloy pipe can be formed by a hot working and/or cold working, keeping at 500° C. or higher and rapidly quenching, and then aging treatment at different temperatures in respective regions. The aging treatment temperature is preferably 250–350° C. in the body portion 42a, and lower than 250° C. in the tip end portion 42c. The aging treatment temperature in the intermediate portion 42b is between those of the body portion 42a and the tip end portion 42c. When gradient is necessary in each region, the aging treatment temperature should gradually decrease in a direction from the base end 43 to the tip end 44 of the catheter in each region.

(ii) Second Embodiment

Figure 16:
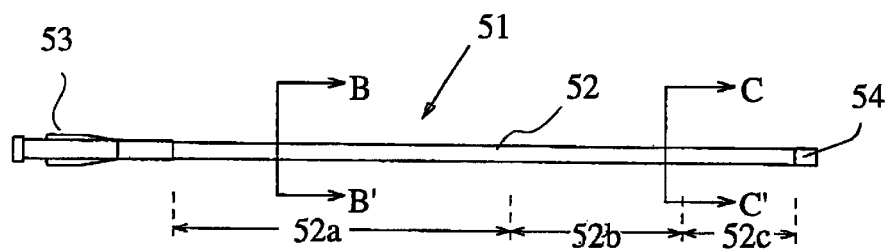
FIG. 16 is a schematic view showing another example of the catheter according to the present invention.
Figure 17:
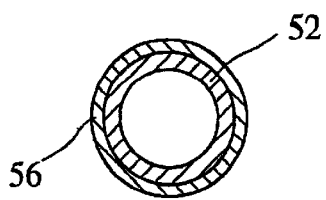
FIG. 17 is an enlarged B–B' cross-sectional view of FIG. 16.
Figure 18:
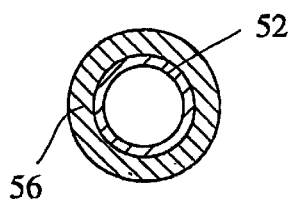
FIG. 18 is an enlarged C–C' cross-sectional view of FIG. 16.

FIG. 16 shows the second example of the catheter of the present invention, FIG. 17 is a B–B' cross-sectional view of FIG. 16, and FIG. 18 is a C–C' cross-sectional view of FIG. 16.

A body of the catheter 51 is constituted by a copper-based alloy pipe 52, which has bending modulus decreasing continuously or stepwise from the base end 53 to the tip end portion 54. The copper-based alloy pipe 52 can be formed from a thicker pipe by gradually reducing its diameter by rolling or drawing. The catheter 51 may be the same as the catheter 41 except that the tip end portion 52c is tapered.

(iii) Third Embodiment

Figure 19:
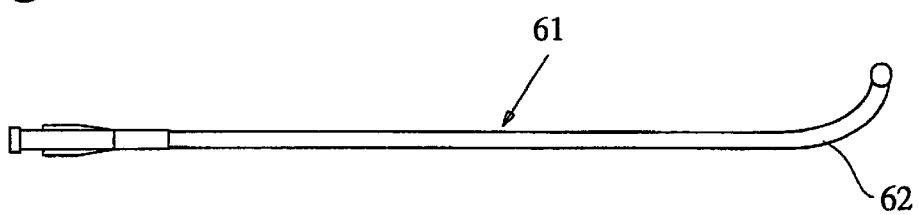
FIG. 19 is a schematic view showing a further example of the catheter according to the present invention.

FIG. 19 shows the third example of the catheter of the present invention. The catheter 61 is bent at an angle of 90–150° in a tip end portion 62 so that the catheter 61 can easily enter into the winding or branched blood vessel. After bending, the copper-based alloy pipe is subjected to a solution treatment and an aging treatment.

(b) Catheter having copper-based alloy reinforcing member

Figure 23:
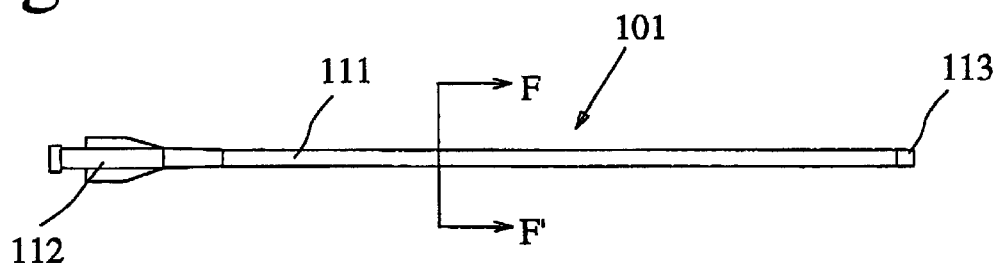
FIG. 23 is a schematic view showing a further example of the catheter according to the present invention.
Figure 24:
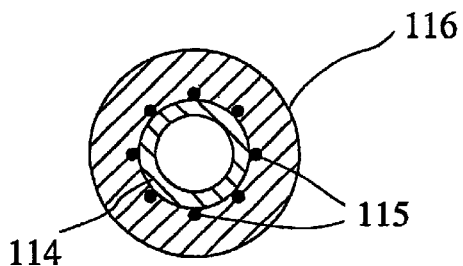
FIG. 24 is an enlarged F–F' cross-sectional view of FIG. 23.

FIG. 23 shows the second catheter of the present invention, and FIG. 24 is an F–F' cross-sectional view of FIG. 23. The catheter 101 is constituted by a flexible tube body 111, a hub 112 mounted to a base end of the flexible tube body 111, and a soft tip 113 mounted to a tip end of the flexible tube body 111. The flexible tube body 111 is preferably reinforced by wire- or ribbon-shaped, reinforcing copper-based alloy members 115.

In an example shown in FIG. 24, the tube body 111 is constituted by an inner layer 114, an intermediate Cu—Al—Mn alloy braid layer 115, and an outer layer 116. Though the intermediate Cu—Al—Mn alloy braid 115 is constituted by 8 thin Cu—Al—Mn alloy wires in FIG. 24, the number of thin wires is not restrictive. Also, a plurality of straight copper-based alloy wires may be disposed along the length of the catheter 101. Also, the copper-based alloy wires may be in the form of coil.

The copper-based alloy reinforcing member has bending modulus decreasing continuously or stepwise from the base end to the tip end. Thus, the body portion is a high-rigidity region, the tip end portion is a low-rigidity, superelastic region, and the intermediate portion is a region having an intermediate rigidity between that of the body portion and that of the tip end portion. In each region, rigidity may be uniform or gradually changing.

Such gradient-rigidity, reinforcing copper-based alloy member can be obtained by an aging treatment at different temperatures in respective regions in the same manner as above.

The catheter containing the reinforcing metal member can be produced by coextrusion of a resin for the tube body 111 and a reinforcing metal member, or by immersing an inner layer 114 coated with the reinforcing metal member 115 in a resin solution and solidifying the resin to form an outer layer 116.

[6] Surface Treatment

The copper-based alloy members such as core wires, guide wires and catheters are preferably coated with Au, Pt, Ti, Pd or TiN by plating or vapor deposition. Also, they are preferably coated with polyethylene, polyvinyl chloride, polyesters, polypropylene, polyamides, polyurethane, polystyrene, fluoroplastics, silicone rubbers or their elastomers, or composites thereof. These coating materials preferably contain X-ray contrast media such as barium sulfate. Further, surfaces of the core wires, the guide wires and the catheters are preferably coated with lubricating materials such as polyvinyl pyrrolidone, ethyl maleate, methyl vinyl ether-maleic anhydride copolymer, etc.

The present invention will be described in detail below referring to the following EXAMPLES, without intention of restricting the scope of the present invention defined by the claims attached hereto.

EXAMPLE 1, COMPARATIVE EXAMPLE 1

Figure 2:
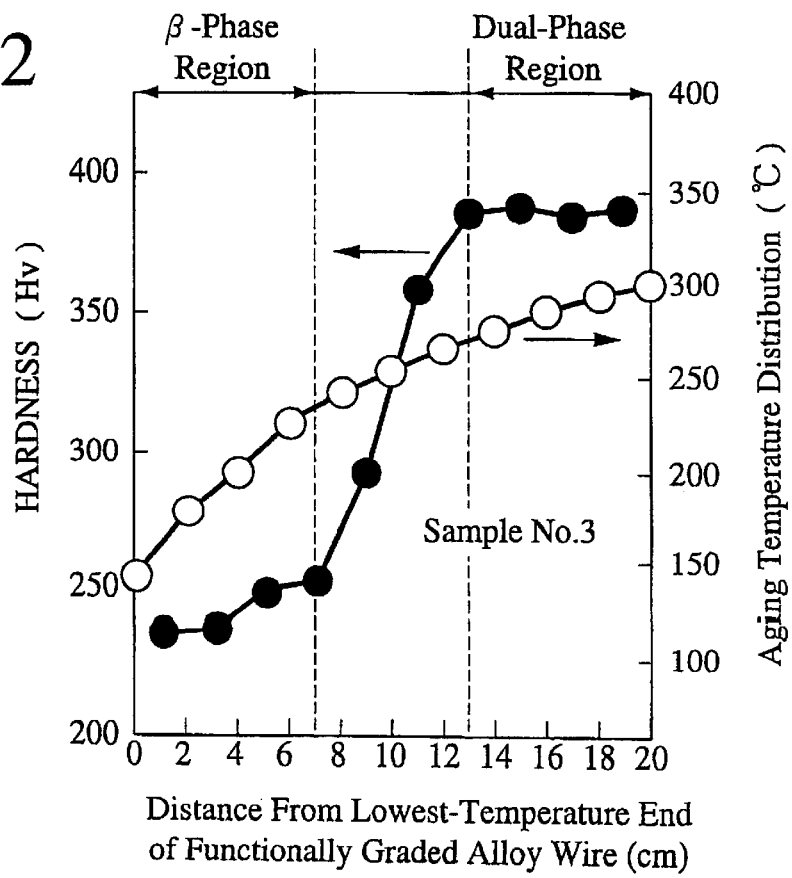
FIG. 2 is a graph showing the hardness distribution and the aging temperature distribution of the functionally graded alloy wire of Sample No. 3 in Example 1.

Copper-based alloys having compositions shown in Table 1 as Sample Nos. 1–7 (EXAMPLE 1) and Sample No. 8 (COMPARATIVE EXAMPLE 1) were melted, and solidified at a cooling rate of 140° C./minute on average to form billets each having a diameter of 20 mm. Each billet was cold-drawn a plurality of times with intermediate annealing to produce a wire having a diameter of 0.5 mm and a length of 200 mm. Each of the resultant wires was heat-treated at 900° C. for 15 minutes, rapidly quenched by immersion in water with ice, and then subjected to an aging treatment by a heater shown in FIG. 1 for 15 minutes, to obtain a functionally graded alloy wire. The temperature distribution of the heater for the aging treatment is 140° C. in a low-aging temperature region and 300° C. in a high-aging temperature region, as shown in FIG. 2.

TABLE 1

Compositions of Functionally graded alloys

| Sample No. | Elements (weight %) | | | |
|---|---|---|---|---|
| | Cu | Al | Mn | Others |
| 1 | Bal. | 8.1 | 9.7 | — |
| 2 | Bal. | 8.7 | 10.6 | — |
| 3 | Bal. | 8.7 | 10.8 | Ti: 0.1, B: 0.05 |
| 4 | Bal. | 8.4 | 10.5 | V: 0.26 |
| 5 | Bal. | 7.6 | 9.7 | V: 0.45 |
| 6 | Bal. | 8.0 | 9.6 | Ni: 1.0 |
| 7 | Bal. | 8.1 | 9.7 | Co: 0.5 |
| 8 | Bal. | 8.0 | 9.5 | Co: 2.4 |

Each wire thus aging-treated was measured with respect to properties described below in a low-aging temperature portion and a high-aging temperature portion to determine property gradient thereof.

(i) Hardness

The harness of each wire was measured both in a low-aging temperature portion and a high-aging temperature portion by a micro-Vickers hardness tester. The measurement results are shown in Table 2.

(ii) Shape recovery ratio

Each wire was wound around a round rod having a diameter of 25 mm in liquid nitrogen, and measured with respect to a curvature radius $R_0$ after taken out of the liquid nitrogen. The curved wire was then heated to 200° C. to recover its original shape, and again measured with respect to a curvature radius $R_1$. The shape recovery ratio Rs of the wire was calculated by the formula: Rs (%)=100×($R_1$-$R_0$)/$R_1$. The calculated shape recovery ratios Rs are shown in Table 2.

(iii) Tensile test

Each wire was subjected to a tensile test according to JIS Z 2241 to measure tensile strength, rupture elongation and yield strength (0.2% offset). The results are shown in Table 3.

TABLE 2

Hardness and shape recovery ratio of functionally graded alloys

| Sample No. | Hardness (Hv) | | Shape recovery Ratio (%) | |
|---|---|---|---|---|
| | L* | H* | L* | H* |
| 1 | 240 | 350 | 83 | 0 |
| 2 | 270 | 380 | 88 | 0 |
| 3 | 235 | 351 | 90 | 0 |
| 4 | 274 | 360 | 85 | 0 |
| 5 | 280 | 370 | 81 | 0 |
| 6 | 258 | 372 | 95 | 0 |
| 7 | 239 | 347 | 94 | 0 |
| 8 | 330 | 391 | 99 | 0 |

Note: *L: Low-aging temperature portion. H: High-aging temperature portion.

TABLE 3

Tensile test results of functionally graded alloys

| Sample No. | Tensile Strength (MPa) | | Rupture Elongation (%) | | 0.2% Offset Yield Strength (MPa) | |
|---|---|---|---|---|---|---|
| | L* | H* | L* | H* | L* | H* |
| 1 | 432 | 1129 | 15.4 | 3.2 | 50 | 807 |
| 2 | 699 | 1074 | 17.2 | 3.3 | 310 | 774 |
| 3 | 639 | 728 | 15.7 | 3.2 | 315 | 544 |
| 4 | 749 | 1147 | 18.2 | 4.6 | 240 | 745 |
| 5 | 272 | 947 | 13.7 | 7.2 | 63 | 539 |
| 6 | 245 | 1032 | 18.2 | 2.7 | 212 | 783 |
| 7 | 529 | 894 | 17.3 | 3.6 | 237 | 717 |
| 8 | 594 | 650 | 2.4 | 0.0 | 370 | Broken |

Note: *L: Low-aging temperature portion. H: High-aging temperature portion.

As is clear from Tables 2 and 3, the properties are remarkably different between the low-aging temperature portion and the high-aging temperature portion. For example, Sample No. 1 exhibits yield stress (0.2% offset yield strength), which is as low as 50 MPa in a low-aging temperature portion and as high as 16 times or more in a high-aging temperature portion. In Sample No. 8 (Comparative Example 1) containing an excess amount of Co, the toughness of the high-aging temperature portion is remarkably deteriorated by the deposition of Co—Al, leading to breakage.

The wire of Sample No. 3 was divided into ten equal parts, and a center portion of each part was measured with respect to hardness. The results are plotted in FIG. 2. As is clear from FIG. 2, the hardness continuously increased from the low-aging temperature portion to the high-aging temperature portion. Particularly in the vicinity of the aging temperature of 250° C., the hardness drastically changed. It was confirmed from the change of hardness that a region extending up to about 7 cm from the low-aging temperature end had a crystal structure substantially composed of β-phase, and that a region extending up to about 7 cm from the high-aging temperature end had a dual-phase crystal structure composed essentially of an α-phase and a Heusler phase. In the intermediate region extending 6 cm between the low-aging temperature region and the high-aging temperature region, the crystal structure was gradually changing.

Figure 3:
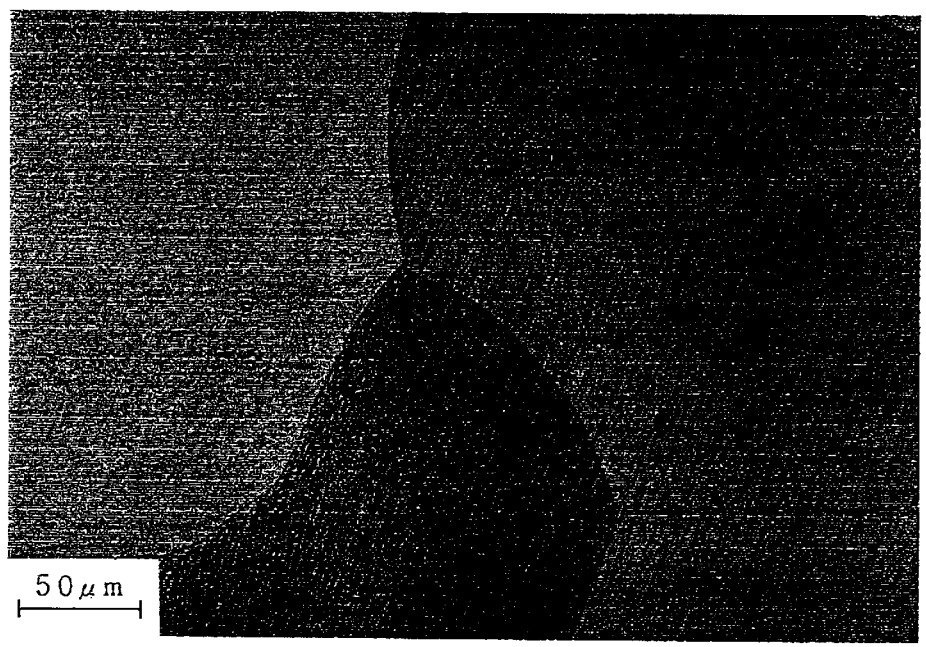
FIG. 3 is an optical photomicrograph showing the microstructure of the low-aging temperature portion of the functionally graded alloy of Sample No. 1 in Example 1.
Figure 4:
FIG. 4 is an optical photomicrograph showing the microstructure of the high-aging temperature portion of the functionally graded alloy of Sample No. 1 in Example 1.

The wire of Sample No. 1 was observed by an optical microscope in both low-aging temperature portion and high-aging temperature portion. FIG. 3 is an optical photomicrograph showing the microstructure of the low-aging temperature portion of the functionally graded alloy of Sample No. 1. As a result of electron diffraction analysis, it was confirmed that the crystal structure of the low-aging temperature portion was composed essentially of a β-phase. FIG. 4 is an optical photomicrograph showing the microstructure of high-aging temperature portion of the functionally graded alloy of Sample No. 1. It was also confirmed by electron diffraction that the microstructure of the high-aging temperature portion was a dual-phase structure of an α-phase and a Heusler phase.

As a result of X-ray diffraction analysis of Sample No. 1, it was confirmed that the low-aging temperature portion was composed of 100 volume % of a β-phase, with 0 volume % of an α-phase and a Heusler phase. It was also confirmed that the high-aging temperature portion was composed of 65 volume % of an α-phase and 35 volume % of a Heusler phase, with a β-phase substantially 0 volume %.

EXAMPLE 2

Copper-based alloys having compositions shown in Table 1 as Sample Nos. 2 and 3 were formed into wires each having a diameter of 0.5 mm and rapidly cooled in the same manner as in Example 1. The resultant copper-based alloy wires were then subjected to an aging treatment at 150° C., 200° C., 250° C., 300° C., 350° C. and 400° C., respectively, each for 15 minutes. The hardness of the aged copper-based alloy wires was measured in the same manner as in Example 1 and plotted in FIG. 5.

Figure 5:
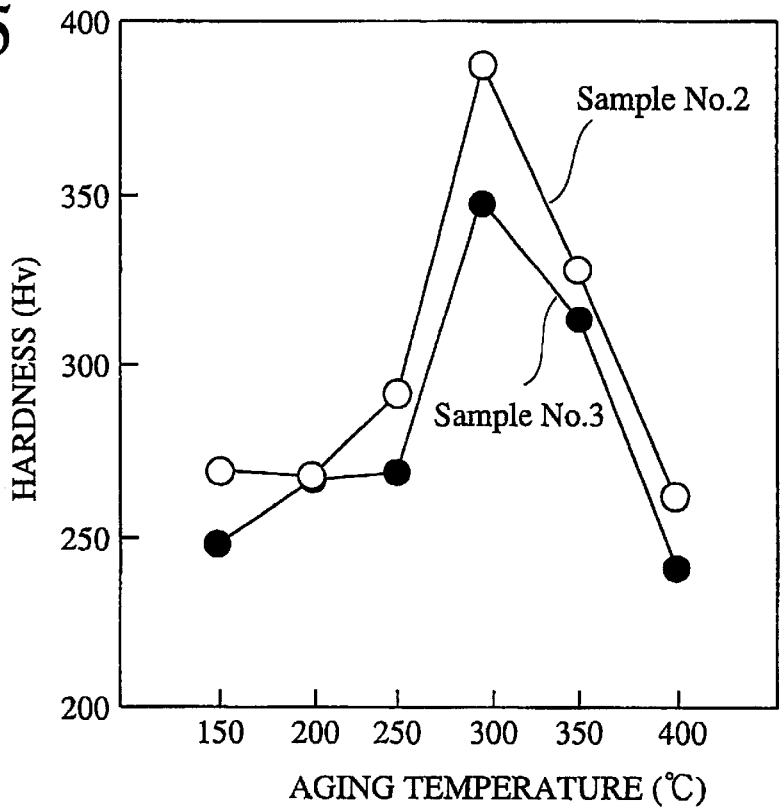
FIG. 5 is a graph showing the relation between the aging temperature and the hardness of Sample Nos. 2 and 3 in Example 2.

As is clear from FIG. 5, the hardness of the copper-based alloys rapidly increased when the aging temperature exceeded 250° C. However, the hardness of the copper-based alloys remarkably decreased when the aging temperature exceeded 350° C.

EXAMPLE 3

Copper-based alloys having compositions shown in Table 1 as Sample Nos. 5 and 6 were formed into wires each having a diameter of 0.5 mm and rapidly cooled in the same manner as in Example 1. The resultant copper-based alloy wires were subjected to an aging treatment at 300° C. for 5, 15, 60, 200, 700, 4500 and 10000 minutes, respectively. The hardness of the aged copper-based alloy wires was measured in the same manner as in Example 1 and plotted in FIG. 6.

Figure 6:
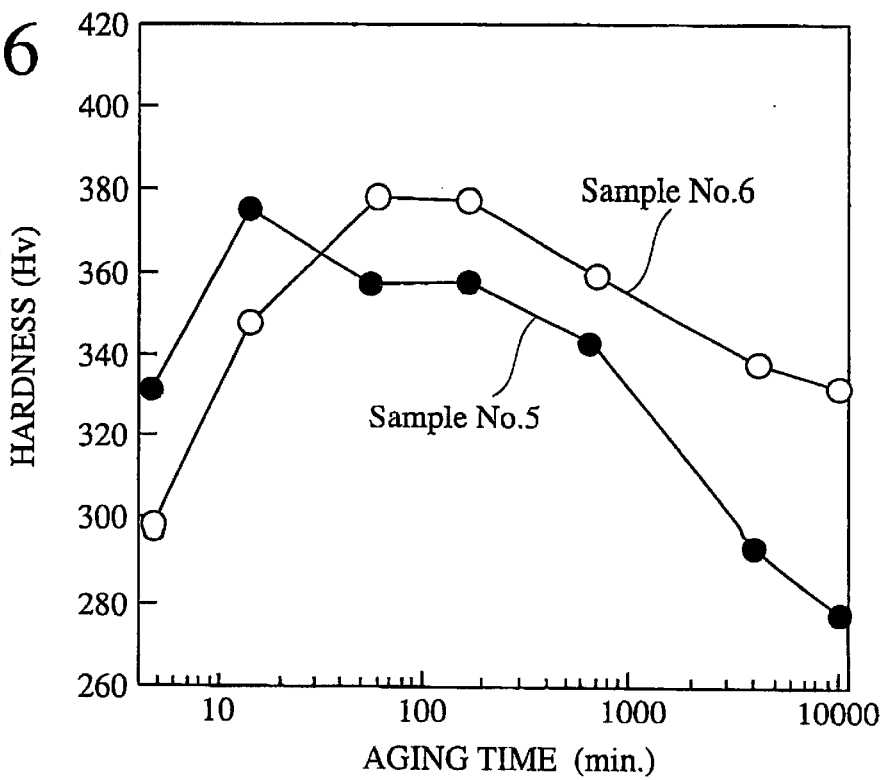
FIG. 6 is a graph showing the relation between the aging time and the hardness of Sample Nos. 5 and 6 in Example 3.

As is clear from FIG. 6, in Sample No. 5 containing V and Sample No. 6 containing Ni, the highest hardness was obtained for an aging time of 5–700 minutes.

EXAMPLE 4

A copper-based alloy wire as shown in FIG. 7 was produced to provide a core wire 2 for a guide wire. The core wire 2 had a total length of 1200 mm, and its tip end 4 was not tapered.

For this purpose, a copper-based alloy comprising 7.5 weight % of Al, 9.9 weight % of Mn, 2.0 weight % of Ni, and 80.6 weight % of Cu was melted, solidified at a cooling speed of 140° C./min. on average, and then cold-drawn to provide a wire of 0.4 mm in diameter. Thereafter, the wire was heat-treated at 900° C. for 10 minutes and rapidly quenched by immersion in ice water.

The resultant core wire 2 was cut to 1200 mm, and subjected to an aging treatment at different temperatures in four regions from the base end 3 to the tip end 4 for 15 minutes; at 300° C. in a region 2a of 600 mm, at 250° C. in a region 2b of 300 mm, at 200° C. in a region 2c of 200 mm, and at 150° C. in a region 2d of 100 mm, respectively. With this heat treatment, the rigidity of the core wire 2 decreased from the base end 3 to the tip end 4. The hardness of each region was measured by a micro-Vickers hardness tester. The measurement results are shown in Table 4.

TABLE 4

Hardness distribution

| Region | Hardness (Hv) |
|---|---|
| 2a | 380 |
| 2b | 290 |
| 2c | 240 |
| 2d | 235 |

It has been found that the Cu—at least—Mn alloy composing the core wire 2 can be provided with different properties at as small intervals as a few centimeters by heating conditions of the aging treatment. Thus, without tapering, a good balance of rigidity and softness can be achieved continuously along the core wire 2. Also, the core wire 2 is an integral wire made of an alloy of the same composition, which is excellent in torque conveyance.

EXAMPLE 5

Figure 10:
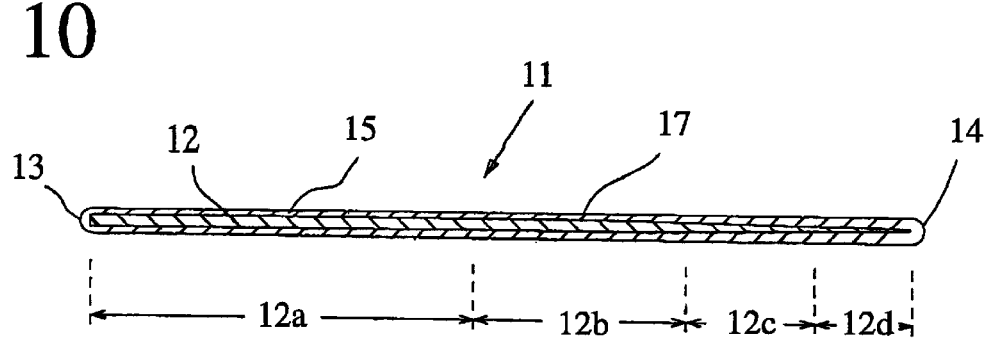
FIG. 10 is an enlarged cross-sectional view showing another example of the guide wire according to the present invention.

A guide wire 11 was produced by using a copper-based alloy wire as shown in FIG. 10 as a core wire 12. The core wire 12 constituted by four regions 12a (500 mm), 12b (100 mm), 12c (50 mm) and 12d (50 mm) from the base end 13 to the tip end 14 was tapered from the region 12c to the tip end 14, such that the regions 12a, 12b had a diameter of 0.4 mm, and that the tip end 14 had a diameter of 0.1 mm. The core wire 12 was subjected to the same aging treatment as in EXAMPLE 4 under the following aging conditions: at 300° C. for the region 12a, at 250° C. for the region 12b, at 200° C. for the region 12c, and at 150° C. for the region 12d. The aging time was 15 minutes. With this aging treatment, the rigidity of the core wire 12 decreased from the base end 13 to the tip end 14.

The resultant core wire 12 was plated with gold, and coated with a polyamide elastomer layer 15 containing 40 weight % of barium sulfate as an X-ray contrast medium. Further, to improve lubrication at the time of insertion into the blood vessel, a surface of the coating layer 15 was covered by a lubricating layer 17 based on polyvinyl pyrrolidone.

EXAMPLE 6

Figure 11:
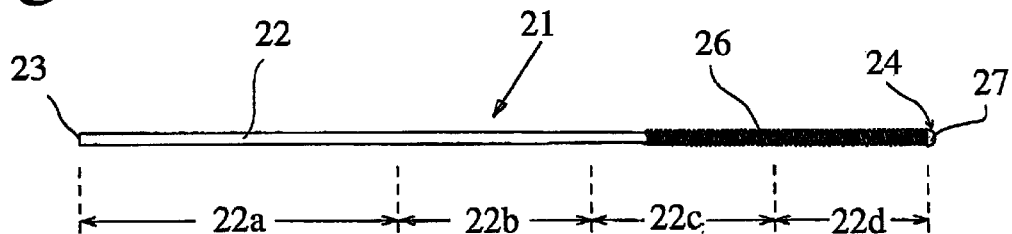
FIG. 11 is a schematic view showing a further example of the guide wire according to the present invention.

A guide wire 21 as shown in FIG. 11 was produced. A core wire 22 constituted by four regions 22a (500 mm), 22b (100 mm), 22c (50 mm) and 22d (50 mm) from the base end 23 to the tip end 24 was tapered from the region 22c to the tip end 24, such that the regions 22a, 22b had a diameter of 0.4 mm, and that the tip end 24 had a diameter of 0.1 mm. The core wire 22 was subjected to the same aging treatment as in EXAMPLE 4 under the following aging conditions: at 300° C. for the region 22a, at 250° C. for the region 22b, at 200° C. for the region 22c, and at 150° C. for the region 22d. The aging time was 15 minutes. With this aging treatment, the rigidity of the core wire 22 decreased from the base end 23 to the tip end 24.

The tapered portion of the resultant core wire 22 was covered by a coil 26, and the tip end 24 was provided with an expanded portion 27 by a plasma welding to avoid damaging of the blood vessel walls. The core wire 22 and the coil 26 were plated with gold. To improve lubrication at the time of insertion into the blood vessel, a surface of the gold plating was covered by a lubricating layer (not shown) based on polyvinyl pyrrolidone.

EXAMPLE 7

Figure 12:
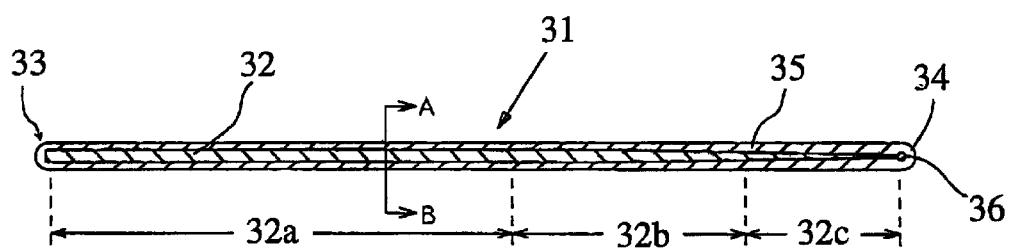
FIG. 12 is an enlarged cross-sectional view showing a further example of the guide wire according to the present invention.
Figure 13:
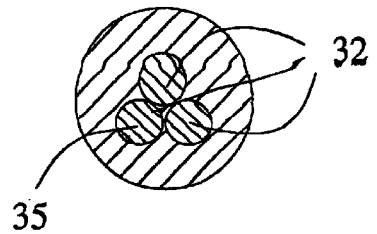
FIG. 13 is an A–B cross-sectional view of FIG. 12.

A core wire 32 of a guide wire 31 as shown in FIG. 12 was a braided wire constituted by three thin copper-based alloy wires. See FIG. 13, an A–B cross section of FIG. 12. The core wire 32 had rigidity stepwise decreasing along a region 32a (500 mm), a region 32b (100 mm) and a region 32c (50 mm) from the base end 33 to the tip end 34. The core wire 32 was tapered from the region 32c to the tip end 34, such that a diameter was 0.4 mm in the regions 32a, 32b and 0.1 mm at the tip end 34. The tip end 34 was provided with an expanded portion 36 by a plasma welding to avoid loosing of the braided wires and to improve the X-ray contrast of the tip end 34.

The core wire 32 was subjected to the same aging treatment as in EXAMPLE 4 except for the following aging conditions: at 300° C. for the region 32a, at 250° C. for the region 32b, and at 200° C. for the region 32c. The aging time was 15 minutes. With this aging treatment, the rigidity of the core wire 32 decreased from the base end 33 to the tip end 34.

The resultant core wire 32 was coated with a polyamide elastomer layer 35 containing 40 weight % of barium sulfate as an X-ray contrast medium. Further, to improve lubrication at the time of insertion into the blood vessel, a surface of the coating layer 35 was covered by a lubricating layer (not shown) based on polymethyl vinyl ether-maleic anhydride derivative.

EXAMPLE 8

A catheter as shown in FIGS. 14 and 15 was produced. The catheter 41 was constituted by a superelastic Cu—Al—Mn alloy pipe 42 having an outer diameter of 1.5 mm and an inner diameter of 1.4 mm. The pipe 42 had bending modulus decreasing stepwise from a body portion 42a to a tip end portion 42c through an intermediate portion 42b, and the tip end portion 42c became gradually softer toward the tip end 44.

For this purpose, a copper-based alloy comprising 7.5 weight % of Al, 9.9 weight % of Mn, 2.0 weight % of Ni, and 80.6 weight % of Cu was melted, solidified at a cooling speed of 140° C./min. on average, and then cold-rolled to provide a pipe of 2 mm in diameter and 0.1 mm in thickness. Thereafter, the pipe was heat-treated at 900° C. for 10 minutes and rapidly quenched by immersion in ice water.

The resultant pipe 42 was subjected to an aging treatment at different temperatures in three regions for 15 minutes; at 300° C. in a region 42a, at 250° C. in a region 42b, and at a temperature gradually decreasing from 200° C. to 150° C. in a region 42c, respectively. The pipe 42 was coated with a polyamide elastomer layer 46 containing 40 weight % of barium sulfate as an X-ray contrast medium and then with a polyvinyl pyrrolidone-based lubricating layer (not shown).

The resultant catheter 41 was rigid in a body portion 42a and fully soft in a tip end portion 42c, making sure safe use for practical applications. It is also possible to improve softness in the tip end portion 42c without tapering. Particularly in a microcatheter having a small diameter, its inner bore can be made relatively large, ensuring easy and safe injection of X-ray contrasting medium, etc.

EXAMPLE 9

A catheter as shown in FIGS. 16–18 was produced. The catheter 51 was constituted by a superelastic Cu—Al—Mn—V alloy pipe 52 having an outer diameter of 1.5 mm and an inner diameter of 1.4 mm. The pipe 52 had bending modulus decreasing stepwise from a body portion 52a to a tip end portion 52c through an intermediate portion 52b, and the tip end portion 52c was tapered such that it became gradually softer toward the tip end.

For this purpose, a copper-based alloy comprising 7.5 weight % of Al, 9.9 weight % of Mn, 2.0 weight % of V, and 80.6 weight % of Cu was melted, solidified at a cooling speed of 140° C./min. on average, and then cold-rolled to provide a pipe of 2 mm in diameter and 0.1 mm in thickness. Thereafter, the pipe was heat-treated at 900° C. for 10 minutes and rapidly quenched by immersion in ice water.

The resultant pipe 52 was subjected to an aging treatment at different temperatures in three regions for 15 minutes; at 300° C. in a region 52a, at 250° C. in a region 52b, and at 150° C. in a region 52c, respectively. The pipe 52 was then coated with a polyamide elastomer layer 56 containing 40 weight % of barium sulfate as an X-ray contrast medium. The pipe 52 was provided with a soft tip 54 at the tip end to prevent the blood vessel walls from being damaged at the time of insertion. Like in EXAMPLE 8, the pipe 52 was coated with a polyvinyl pyrrolidone-based lubricating layer (not shown) from the intermediate portion 52b to the tip end to increase lubrication at the time of insertion into the blood vessel.

The resultant catheter 51 was rigid in a body portion 52a and fully soft in a tip end portion 52c, making sure safe use for practical applications. Because this catheter 51 has properties changing from the body portion 52a to the tip end portion 52c, and because the tip end portion 52c is tapered toward the tip end, it has wide versatility in design with a rigid body portion and a soft tip end portion.

EXAMPLE 10

A catheter as shown in FIG. 19 was produced in the same manner as in EXAMPLE 9. The catheter 61 was the same as in EXAMPLE 9 except that a tip end portion 62 of the catheter 61 was bent at about 120°. This catheter 61 could easily be inserted into the winding or branched blood vessels.

EXAMPLE 11

Figure 20:
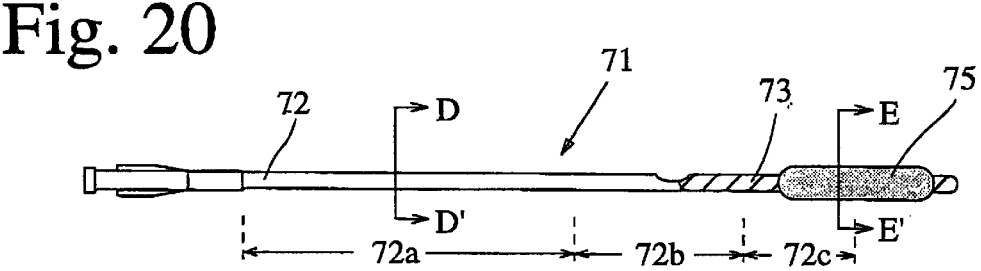
FIG. 20 is a schematic view showing a further example of the PTCA catheter equipped with a balloon according to the present invention.
Figure 21:
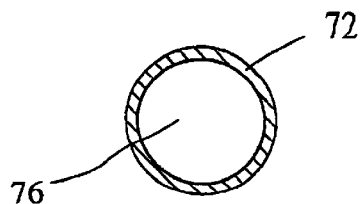
FIG. 21 is an enlarged D–D' cross-sectional view of FIG. 20.
Figure 22:
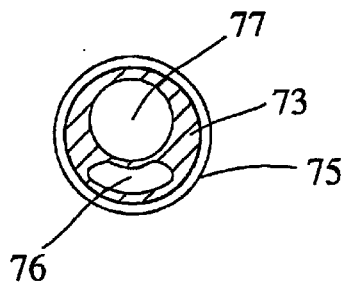
FIG. 22 is an enlarged E–E' cross-sectional view of FIG. 20.

A PTCA catheter 71 equipped with a balloon as shown in FIGS. 20–22 was produced from the same Cu—Al—Mn—Ni alloy as in EXAMPLE 8 in the same manner as in EXAMPLE 9. The catheter 71 was constituted by a Cu—Al—Mn—Ni alloy pipe 72 having a diameter of 2 mm and a thickness of 0.1 mm. The pipe 72 had rigidity decreasing stepwise from a body portion 72a to a tip end portion 72c through an intermediate portion 72b, and the tip end portion 72c was tapered to become gradually softer toward the tip end.

The resultant pipe 72 was plated with gold and covered by a polyamide elastomer tube 73 in the tip end portion 72c. The elastomer tube 73 had a through-hole 76 for allowing a balloon 75 to inflate, and a through-hole 77 extending from a halfway of the catheter 71 to the tip end portion for allowing a guide wire to pass through. Because the Cu—Al—Mn alloy pipe 72 extends almost up to a balloon region along the catheter 71, the catheter 71 has full rigidity while showing excellent softness and kink resistance, ensuring safe use.

EXAMPLE 12

A catheter as shown in FIGS. 23 and 24 was produced. The catheter 101 was constituted by a tube body 111, a hub 112 mounted to a base end of the tube body 111, and a soft tip 113 mounted to a tip end of the tube body 111. The tube body 111 was constituted by an inner layer 114, an intermediate Cu—Al—Mn alloy braid layer 115, and an outer layer 116 as shown in FIG. 24. The intermediate Cu—Al—Mn alloy braid 115 was constituted by eight 0.035-mm-thick Cu—Al—Mn alloy wires comprising 7.5 weight % of Al, 9.9 weight % of Mn, 2.0 weight % of Ni, and 80.6 weight % of Cu. The thin Cu—Al—Mn alloy wires were produced in the same manner as in EXAMPLE 9. The Cu—Al—Mn alloy braid 115 was coextruded with nylon 12 to form the catheter 101 having the Cu—Al—Mn alloy braid 115 embedded in the tube body 111.

EXAMPLE 13

Figure 25:
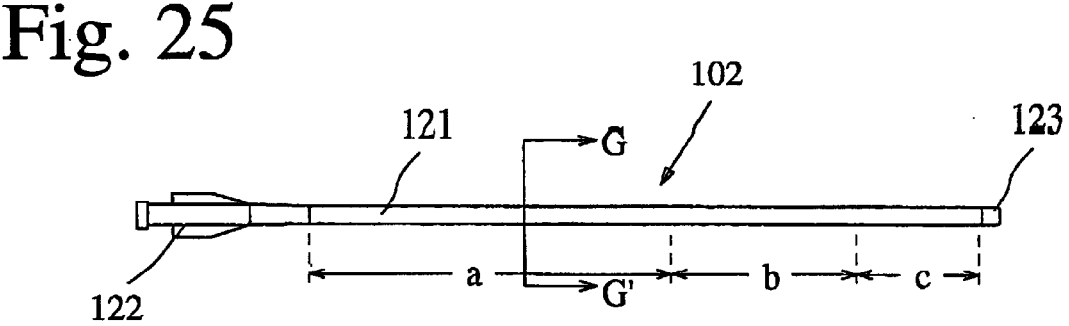
FIG. 25 is a schematic view showing a further example of the catheter according to the present invention.
Figure 26:
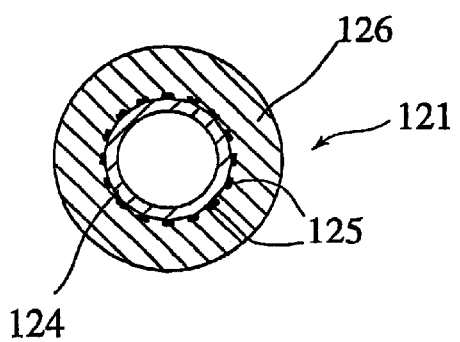
FIG. 26 is an enlarged G–G' cross-sectional view of FIG. 25.

A catheter as shown in FIGS. 25 and 26 was produced. The catheter 102 was constituted by a tube body 121, a hub 122 mounted to a base end of the tube body 121, and a soft tip 123 mounted to a tip end of the tube body 121. The tube body 121 was constituted by an inner layer 124, an intermediate Cu—Al—Mn alloy braid layer 125, and an outer layer 126 as shown in FIG. 26. The intermediate Cu—Al—Mn—V alloy braid 125 was constituted by 32 thin Cu—Al—Mn—V alloy wires having a thickness of 0.02 mm comprising 8.0 weight % of Al, 10.2 weight % of Mn, 1.0 weight % of V, and 80.8 weight % of Cu. The Cu—Al—Mn—V alloy braid 125 was subjected to an aging treatment at 300° C. in a region a, at 250° C. in a region b and at 150° C. in a region c for 15 minutes, so that the regions a, b and c had rigidity decreasing in this order. The Cu—Al—Mn—V alloy braid 115 was coextruded with a polyurethane resin in the same manner as in EXAMPLE 12 to form a catheter 102 having the Cu—Al—Mn—V alloy braid 125 embedded in the tube body 121.

EXAMPLE 14

Figure 27:
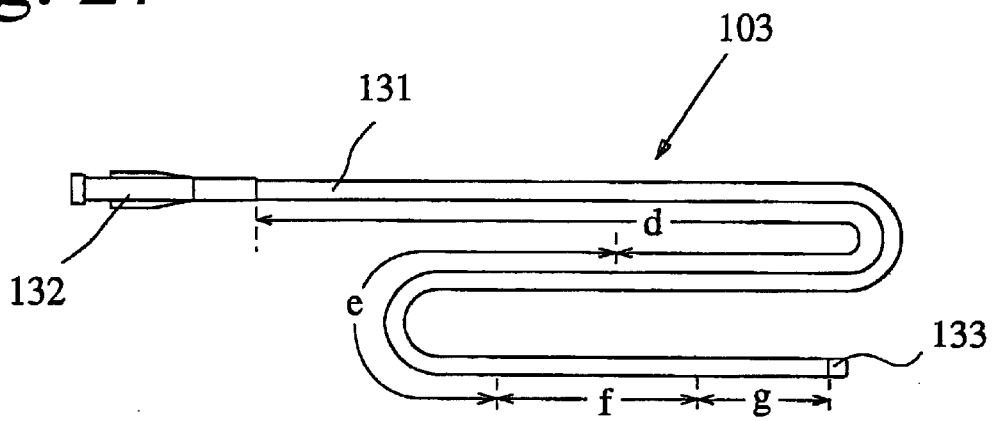
FIG. 27 is a schematic view showing a further example of the catheter according to the present invention.
Figure 28:
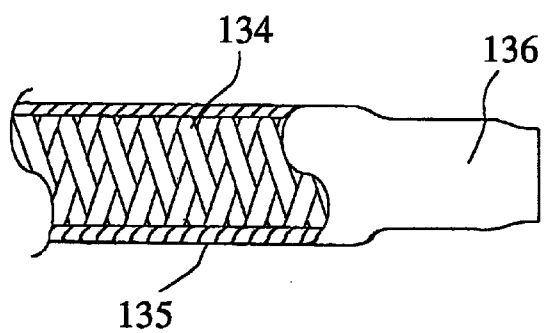
FIG. 28 is a partial enlarged cross-sectional view of FIG. 27.

A catheter as shown in FIGS. 27 and 28 was produced. The catheter 103 was constituted by a tube body 131, a hub 132 mounted to a base end of the tube body 131, and a soft tip 133 mounted to a tip end of the tube body 131. The tube body 131 was constituted by an inner layer 134, an intermediate Cu—Al—Mn alloy braid layer 135, and an outer layer 136 as shown in FIG. 28. The intermediate Cu—Al—Mn—V alloy braid 135 was constituted by two spirally crossing Cu—Al—Mn—V alloy ribbons each having a thickness of 0.01 mm comprising 8.0 weight % of Al, 10.2 weight % of Mn, 1.0 weight % of V, and 80.8 weight % of Cu. The Cu—Al—Mn—V alloy braid 135 was subjected to an aging treatment at temperatures shown in Table 5 below for 15 minutes so that regions d, e, f and g had rigidity decreasing in this order. The hardness of the braid 135 in each region was measured by a micro-Vickers hardness tester. The measurement results are shown in Table 5.

TABLE 5

| Region | Aging Temperature (° C.) | Hardness (Hv) |
|---|---|---|
| d | 300 | 380 |
| e | 250 | 290 |
| f | 200 | 260 |
| g | 150 | 270 |

The Cu—Al—Mn—V alloy braid 135 was coextruded with nylon 12 in the same manner as in EXAMPLE 12 to form a catheter 103 having the Cu—Al—Mn—V alloy braid 135 embedded in the tube body 131.

EXAMPLE 15

Figure 29:
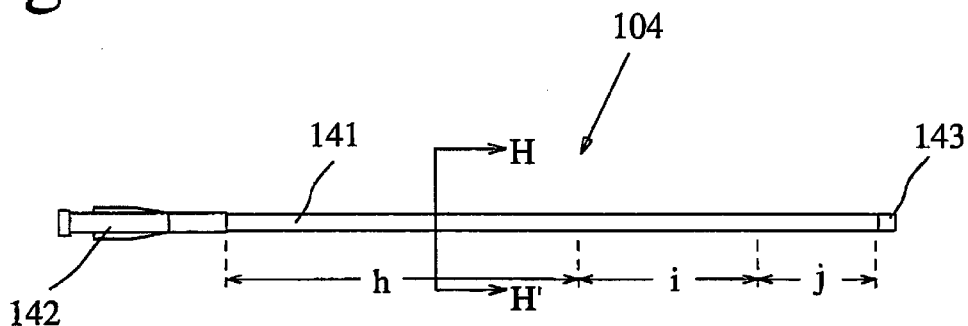
FIG. 29 is a schematic view showing a further example of the catheter according to the present invention.
Figure 30:
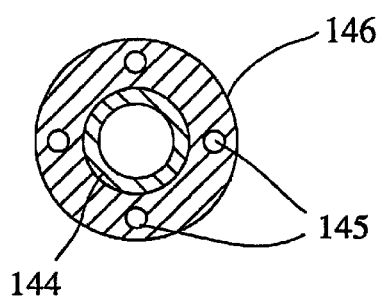
FIG. 30 is an enlarged H–H' cross-sectional view of FIG. 29.

A catheter as shown in FIGS. 29 and 30 was produced. The catheter 104 was constituted by a tube body 141, a hub 142 mounted to a base end of the tube body 141, and a soft tip 143 mounted to a tip end of the tube body 141. The tube body 141 was constituted by an inner layer 144, four intermediate wires 145 made of the same Cu—Al—Mn—V alloy as in EXAMPLE 13, and an outer layer 146. The Cu—Al—Mn—V alloy wires 145 were subjected to an aging treatment at 300° C. in a region h, at 250° C. in a region i and at 150° C. in a region j for 15 minutes, so that the regions h, i and j had rigidity decreasing stepwise in this order. Also, the catheter 104 was tapered from a halfway of the region i to the tip end to ensure softness.

EXAMPLE 16

Figure 31:
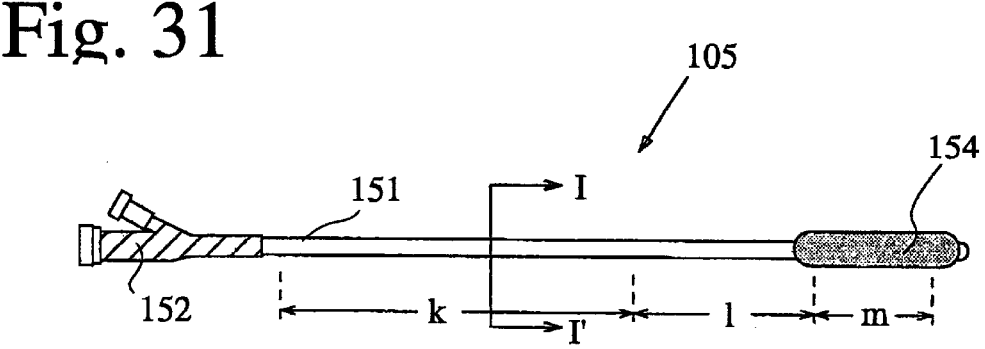
FIG. 31 is a schematic view showing a further example of the catheter according to the present invention.
Figure 32:
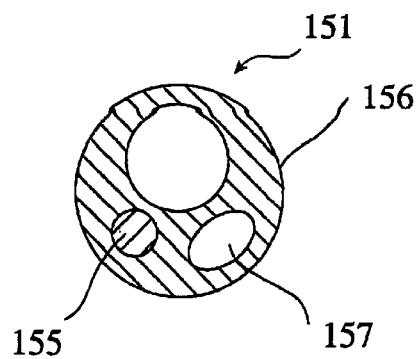
FIG. 32 is an enlarged I–I' cross-sectional view of FIG. 31.

A catheter as shown in FIGS. 31 and 32 was produced in the same manner as in EXAMPLE 13. The catheter 105 was constituted by a tube body 151, a Y-shaped hub 152 mounted to a base end of the tube body 151, and a balloon 154 mounted to a tip end of the tube body 151. The tube body 151 had a hole 157 for inflating the balloon 154, a thin Cu—Al—Mn alloy wire 155 and an outer layer 156. The Cu—Al—Mn alloy wire 155 was subjected to an aging treatment at 300° C. in a region k, at 250° C. in a region l and at 150° C. in a region m for 15 minutes, so that the regions k, l and m had rigidity decreasing stepwise in this order. Also, the catheter 105 was tapered from a halfway of the region m to the tip end to ensure softness.

As described above in detail, the functionally graded alloy of the present invention exhibits drastically changing properties such as shape recovery properties, superelasticity, hardness, mechanical strength, etc., without mechanical working such as cutting or chemical treatment such as etching for imparting size gradient. Such a functionally graded alloy can be easily produced at low cost from a copper-based alloy composed essentially of a β-phase, by an aging treatment in a heater having a continuous or stepwise temperature gradient. The functionally graded alloy of the present invention can be formed into various shapes because of its excellent cold workability.

When the core wire, the guide wire or the catheter is constituted by a copper-based alloy having gradient properties according to the present invention, it is provided with optimum rigidity and toughness in a body portion and proper softness in a tip end portion without mechanical or chemical working. Such core wire, guide wire or catheter is excellent in insertion operability and torque conveyance, and can be inserted and placed at a desired spot in the blood vessel without damaging walls thereof.

What is claimed is:

1. A functionally graded alloy having a composition comprising 3–10 weight % of Al, 5–20 weight % of Mn, the balance being substantially Cu and inevitable impurities, wherein said functionally graded alloy comprises a first portion composed essentially of a β-phase, a second portion composed essentially of an α-phase and a Heusler phase, and a third portion having a crystal structure changing continuously or stepwise from said first portion to said second portion.

2. The functionally graded alloy according to claim 1, further containing at least one metal selected from the group consisting of Ni, Co, Fe, Ti, V, Cr, Si, Nb, Mo, W, Sn, Ag, Mg, P, Zr, Zn, B and misch metals in a total amount of 0.001–10 weight %.

3. The functionally graded alloy according to claim 1, wherein said functionally graded alloy is produced from a copper-based alloy having a crystal structure composed essentially of a β-phase by an aging treatment comprising heating said first portion at a temperature of lower than 250° C., said second portion at a temperature of 250–350° C., and said third portion at a temperature continuously or stepwise changing from the heating temperature of said first portion to the heating temperature of said second portion.

4. The functionally graded alloy according to claim 1, wherein said first portion has hardness of 350 Hv or less, said second portion has hardness 20 Hv or more higher than that of said first portion, and said third portion has hardness continuously or stepwise changing from that of said first portion to that of said second portion.

5. The functionally graded alloy according to claim 1, wherein said first portion has a yield stress of 400 MPa or less, said second portion has a yield stress at least 50 MPa higher than that of said first portion, and said third portion has a yield stress continuously or stepwise changing from that of said first portion to that of said second portion.

6. The functionally graded alloy according to claim 1, wherein said first portion has a shape recovery ratio of 80% or more, said second portion has a shape recovery ratio of 15% or less, and said third portion has an shape recovery ratio continuously or stepwise changing from that of said first portion to that of said second portion.

* * * * *